(12) United States Patent
Gellis et al.

(10) Patent No.: US 7,735,154 B2
(45) Date of Patent: Jun. 15, 2010

(54) PROTECTIVE EAR APPLIANCE

(75) Inventors: David Gellis, Stowe, VT (US); Gad Shaanan, La Jolla, CA (US); Francois Duval, Terrebonne (CA); Serge Dubeau, Laval (CA); Ivan Brousseau, Montreal (CA)

(73) Assignee: Gordini USA Inc., Essex Junction, VT (US)

( * ) Notice: Subject to any disclaimer, the term of this patent is extended or adjusted under 35 U.S.C. 154(b) by 0 days.

(21) Appl. No.: 11/154,935

(22) Filed: Jun. 15, 2005

(65) Prior Publication Data

US 2006/0000006 A1    Jan. 5, 2006

Related U.S. Application Data

(60) Provisional application No. 60/579,906, filed on Jun. 15, 2004.

(51) Int. Cl.
*A42B 1/06* (2006.01)
(52) U.S. Cl. .............................................. 2/209; 2/410
(58) Field of Classification Search ................ 2/209, 2/423, 203, 417; 381/309, 72; 181/29
See application file for complete search history.

(56) References Cited

U.S. PATENT DOCUMENTS

| | | | | |
|---|---|---|---|---|
| 185,506 A * | 12/1876 | Edgar | ............................. | 2/209 |
| 359,612 A * | 3/1887 | Kleinert | ......................... | 2/209 |
| 360,985 A * | 4/1887 | Basch | ............................ | 2/209 |
| 375,594 A * | 12/1887 | Basch | ............................ | 2/209 |
| 1,398,958 A * | 12/1921 | Basch | ............................ | 2/209 |
| 2,615,169 A * | 10/1952 | Maxant | .......................... | 2/209 |
| 2,782,423 A * | 2/1957 | Simon et al. | .................... | 2/209 |
| 3,787,899 A * | 1/1974 | Krawagna | ....................... | 2/209 |
| 4,048,453 A * | 9/1977 | Seidel | .......................... | 379/430 |
| 4,713,843 A * | 12/1987 | Duncan | .......................... | 2/209 |
| 5,551,090 A * | 9/1996 | Thompson | ...................... | 2/209 |
| 5,898,945 A * | 5/1999 | Weiser | ............................ | 2/209 |
| 6,735,784 B2 | 5/2004 | Isom et al. | | |
| 6,880,174 B2 * | 4/2005 | Prokop | ............................. | 2/209 |
| 6,978,483 B2 | 12/2005 | Isom et al. | | |
| 7,212,645 B2 | 5/2007 | Le Gette et al. | | |
| D545,001 S | 6/2007 | Le Gette et al. | | |
| 2001/0017925 A1* | 8/2001 | Ceravolo | ...................... | 381/370 |
| 2003/0037366 A1* | 2/2003 | Lindgren | ........................ | 2/209 |
| 2005/0034216 A1 | 2/2005 | Le Gette et al. | | |
| 2005/0034218 A1 | 2/2005 | Le Gette et al. | | |
| 2006/0206983 A1 | 9/2006 | Isom et al. | | |

* cited by examiner

*Primary Examiner*—Katherine Moran
*Assistant Examiner*—Richale L Quinn
(74) *Attorney, Agent, or Firm*—Florek & Endres PLLC

(57) ABSTRACT

A protective ear appliance including two ear protectors with a band and a slidable coupling between the band and the ear protectors. The band encircles a portion of a wearer's head, has a curved shape with two ends and inner and outer curved surfaces. There is a slidable coupling between each of the ear protectors and the band so that each ear protector can slide independently with respect to the band to adjust the distance between the two ear protectors along the band so that the ear protectors can seat in the wearer's ears. The band can be formed with a central band hingedly coupled to the two end band portions. The ear protectors are coupled to the end band portions and slide relative to the end band portions. The protective ear appliance is designed to be worn with the central band around the back of the wearer's head.

28 Claims, 8 Drawing Sheets

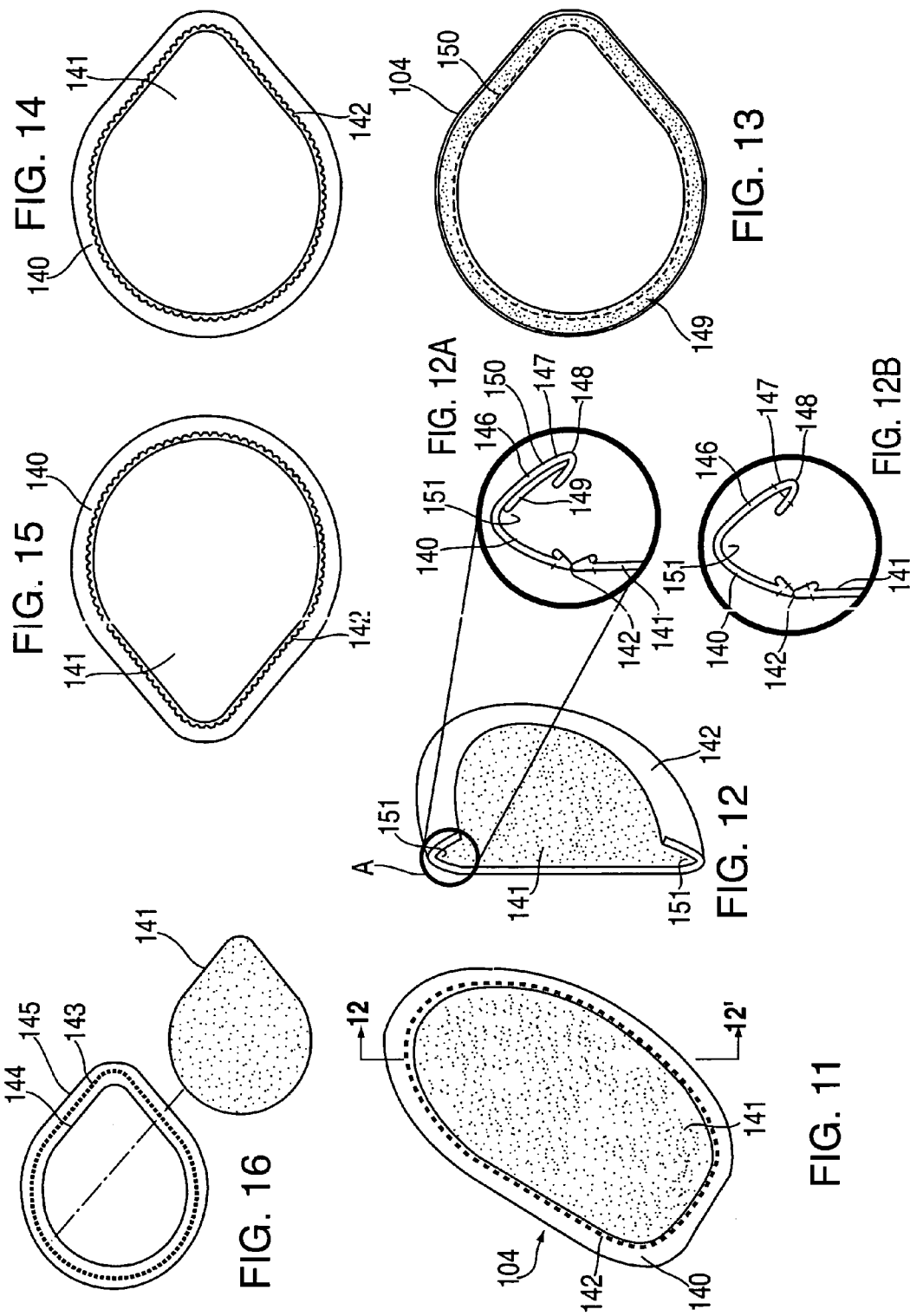

PROTECTIVE EAR APPLIANCE

This application claims the priority of prior Provisional Patent Application Ser. No. 60/579,906 filed on Jun. 15, 2004.

BACKGROUND OF THE INVENTION

The invention is generally directed to a protective ear appliance, and, in particular, to a device, known either an earmuff or ear band, which covers the wearer's ears with cupped regions sized and shaped to cover the ears and a band between the ear cups to support the earmuff or ear band on the wearer's head. In the past, earmuffs have been generally known in which the earmuff band was generally positioned on top of the wearer's head so that gravity provided much of the ability of the earmuff to remain on the wearer's head. However, in many uses it was desired that the band not rest on the wearer's head as this tended to affect the wearer's hair and interfere with wearing a hat, helmet or was generally uncomfortable for the wearer. Of course, the traditional earmuffs were formed with a metal, spring-like band, which provided a gentle biasing force of the ear cups against the wearer's ears and in the vertical orientation this is generally adequate to keep the earmuffs seated during normal walking activities.

However, when the earmuff was rotated approximately 90 degrees so that the connecting band was generally horizontal around the back of the wearer's head or in the neck region, gravity did not assist the earmuff in remaining in place and it became necessary to rely on the biasing force in the band to maintain suitable pressure. Generally, this approach required that the band have greater tension in it, which tended to make the earmuffs less comfortable to wear and made adjustment of the ear band and particularly important as, without a good fit around the wearer's ears of the ear cup, the earmuff was likely to slide or be uncomfortable.

Prior art earmuffs which were designed to be worn with a band around the back of the wearer's head instead of on top of the wearer's head suffer from several problems. First, the adjustment system was contained, as in the prior art, in the band itself, which has the effect of modifying the biasing force in the band applied to the wearer's head. This tends to make the earmuff in some cases too tight so that it is uncomfortable for the wearer and, in other cases, too loose so that the earmuff is likely to slide. In addition, most of these devices have metal which can in certain circumstances be uncomfortable and dangerous in use and require that the frame of the device be enclosed in a pocket or fabric enclosure. In addition, these devices are generally not constructed in a fashion in which the ear cups are protective of the ear apart from providing some insulation and temperature protection.

Accordingly, there is a need for a protective ear appliance which goes around the back of the wearer's head and is adjustable apart from the band so that the biasing force exerted by the band is generally not substantially affected by the adjustment of the size of the protective ear appliance. In addition, there is a need for a protective ear appliance for use around the back of the wearer's head, which provides for a wide range of adjustment of the size through movement of the ear cups independently so that, depending upon the configuration of the wearer's ears on the head, the band can be appropriately seated on the back of the head and the ear cups independently adjustment. There is also a need for the ear cups to be formed in a way which provides greater protection to the wearer's ears against wind and temperature without overheating the ears.

SUMMARY OF THE INVENTION

The invention is generally directed to a protective ear appliance which includes two ear protectors and, for encircling a portion of a wearer's head, having a curved shape, with two ends, an inner curved surface and an outer curved surface. A slidable coupling slidably couples each of the ear protectors to the band so that the ear protectors can each slide independently with respect to the band to adjust the distance between the two ear protectors along the band so that the ear protectors can seat upon the wearer's ears.

Another object of the invention is to provide an improved protective ear appliance which allows the wearer's ears to be covered with the band in the back with adjustment of the length of the protective ear appliance performed between the ends of the band and the ear protectors.

Yet another object of the invention is to provide an improved protective ear appliance in which the ear protector provides a wind-proof barrier utilizing a form-fitted part, together with a fabric cap.

Still another object of the invention is to provide a protective ear appliance adapted to go over the back of the wearer's head, which folds into a storage position when not in use.

Yet another object of the invention is to provide an improved protective ear appliance in which a pair of hinges on the band allow the ear protectors to move between a storage position within the central portion of the band and a deployed position in which the end portions of the band generally continue the curve of the central portion of the band and are adapted for use.

Yet still a further object of the invention is to provide an adjustment system for a protective ear appliance in which an integral slidable coupling means allows independent adjustment of each of the ear protectors relative to the end portions of the band.

Still yet another object of the invention is to provide an improved protective ear appliance in which an additional ear hook is added the ear cups to provide additional stability in the event of high impact or activities.

Still other objects and advantages of the invention will, in part, be obvious and will, in part, be apparent from the specification.

The invention accordingly comprises the features of construction, combinations of elements and arrangements of parts which will be exemplified in the construction as hereinafter set forth, and the scope of the invention will be indicated in the Claims.

BRIEF DESCRIPTION OF THE DRAWINGS

For a fuller understanding of the invention, reference is had to the following description taken in connection with the accompanying drawings, in which:

FIG. 11 is a perspective view of the cap used on the earpiece constructed in accordance with a preferred embodiment of the invention;

FIG. 12 is a cross-sectional view taken along the line 12-12' of FIG. 11;

FIG. 12A is an enlarged view of the circular region labeled A in FIG. 12;

FIG. 12B is an enlarged view of the circular region labeled B in accordance with another preferred embodiment of the invention.

FIG. 13 is a top plan view of the cap of FIG. 11 constructed in accordance with a preferred embodiment of the invention;

FIG. 14 is a bottom plan view of the cap of FIG. 11;

FIG. 15 is a top plan view of the cap of FIG. 11;

FIG. 16 is an unassembled view of the components of the cap of FIG. 11

DETAILED DESCRIPTION OF THE PREFERRED EMBODIMENTS

Figure 1:
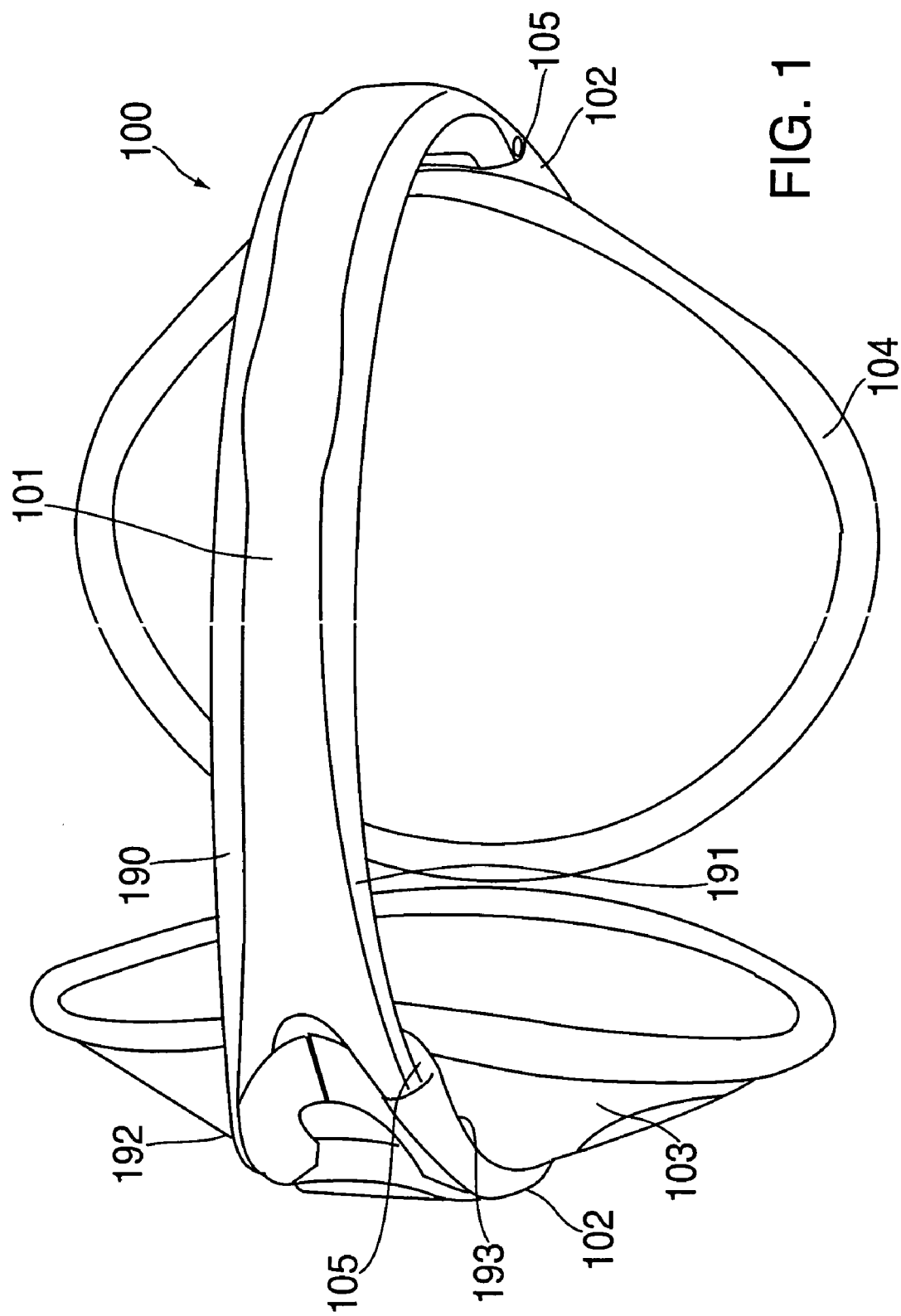
FIG. 1 is a perspective view of a protective ear appliance constructed in accordance with a preferred embodiment of the invention.

References first made to FIG. 1 wherein a protective ear appliance generally indicated as 100 constructed in accordance with a preferred embodiment of the invention is depicted. Protected ear appliance 100 includes a center band 101, two end band sections 102, two ear pieces 103, two caps 104, which fit on ear pieces 103, and two hinges 105 connecting center band 101 with each of end band sections 102. Ear pieces 103 are slidably secured to end band sections 102 and can adjust the relative length of the distance between ear caps 103 around a band sections 101 and 102 by each earpiece being slidably adjustable relative to each of the end band sections 102. Each earpiece 103 is independently adjustable relative to its corresponding end band section 102.

Figure 2:
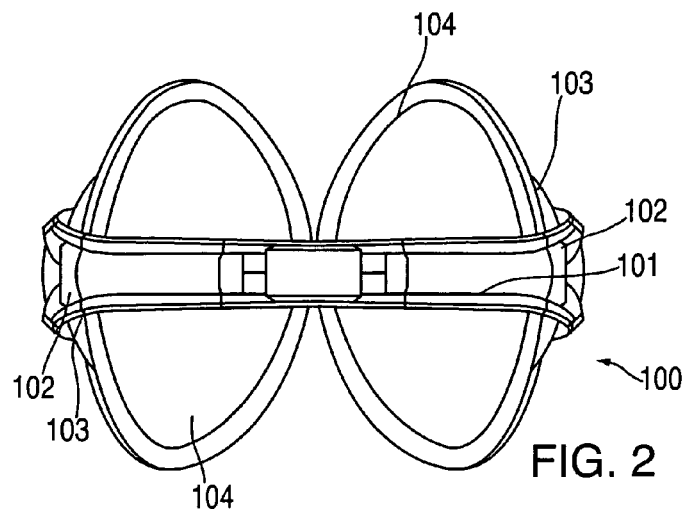
FIG. 2 is a top perspective view of the protective ear appliance constructed in accordance with the invention, similar to FIG. 1.
Figure 3:
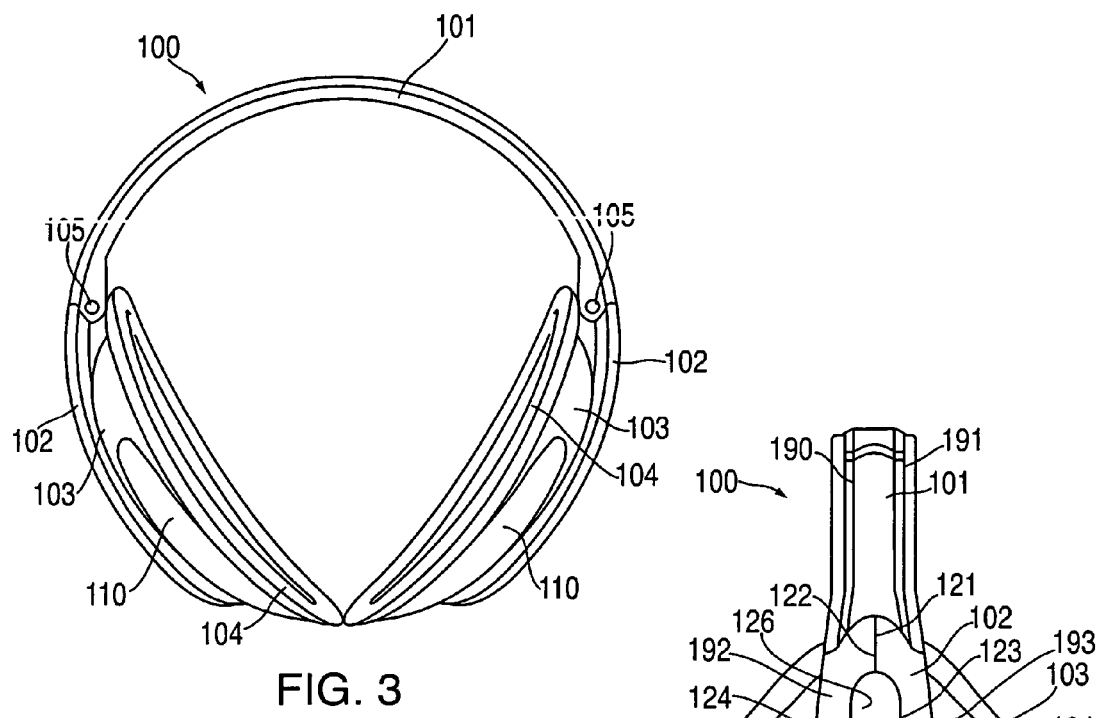
FIG. 3 is a front perspective view of the protective ear appliance of FIG. 1 and FIG. 2.
Figure 4:
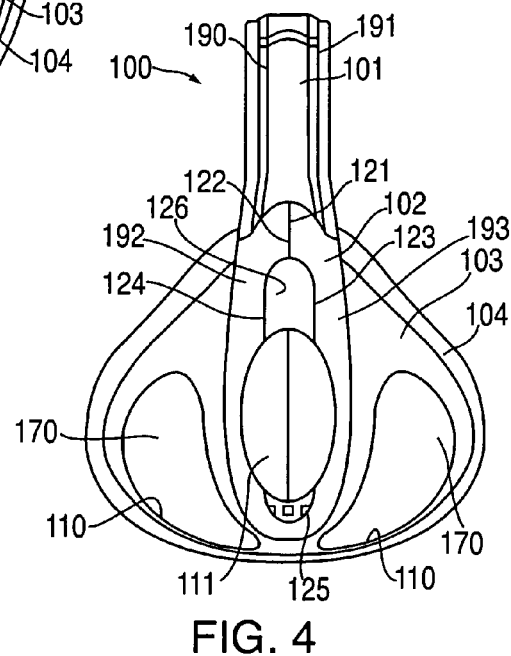
FIG. 4 is a side perspective view of the protective ear appliance of FIGS. 1-3.

Reference is next made to FIGS. 2, 3, and 4, wherein differing views of the protective ear appliance 100 shown in FIG. 1 are depicted. Like reference numerals represent like elements. As seen in FIG. 3, center band 101 and end bands 102 and 103 form a generally continuous curve which leaves earpieces 103 with caps 104 in a position where the bottom ends of earpieces 103 either touch are close to each other. In use, a wearer would have to pull apart earpieces 103 so as to expand the distance between them and then seat caps 104 around the user's ears. Generally, the protective ear appliance 100 is designed to be worn around the back of the wearer's head and the three portions of the band 101 and 102 provide sufficient tension when stretched to the required size so as to maintain the earpieces in place of the wearer's ears. Ribs 190, 191 extend along the length of center band 101 to provide increased rigidity and more tension in the band when it is stretched to cover the wearer's ears. As seen in FIG. 3 end band sections 102 are rotatably connected to center band 101 by hinges 105 which connect these parts. As seen better in FIG. 4, end band sections 102 have a sinusoidally shaped top surface which mates with a correspondingly negative curved shape in center band section 101. The hinge allows rotation perpendicular to the plane of the bands 101 and 102 in FIG. 3 in the direction which is toward the interior of center band 101.

Figure 5:
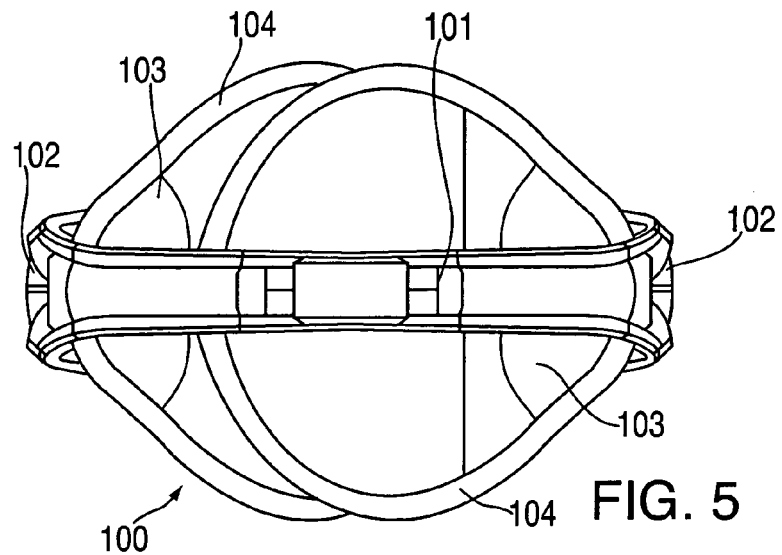
FIG. 5 is a top perspective view similar to FIG. 2 of the same protective ear appliance in accordance with a preferred embodiment of the invention in which the ear pieces are folded in the storage position.
Figure 6:
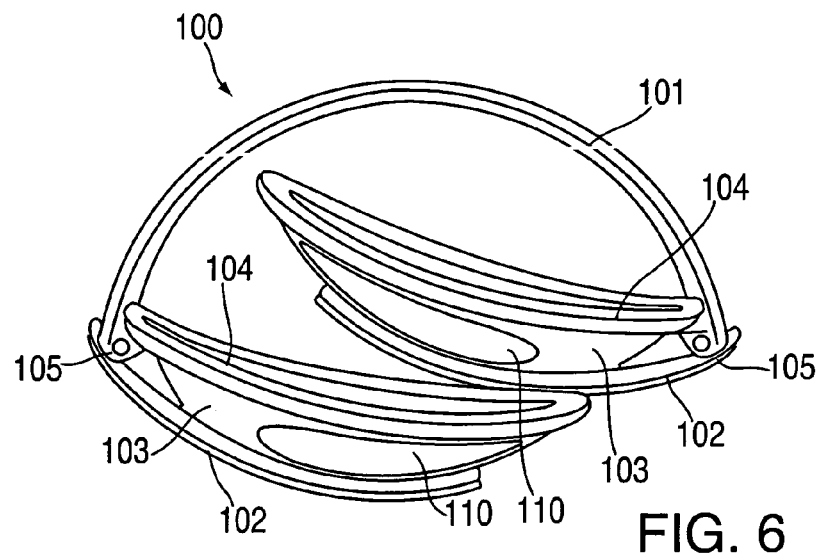
FIG. 6 is a front perspective view similar to FIG. 3 wherein the ear pieces are folded into the storage position as in FIG. 5.
Figure 7:
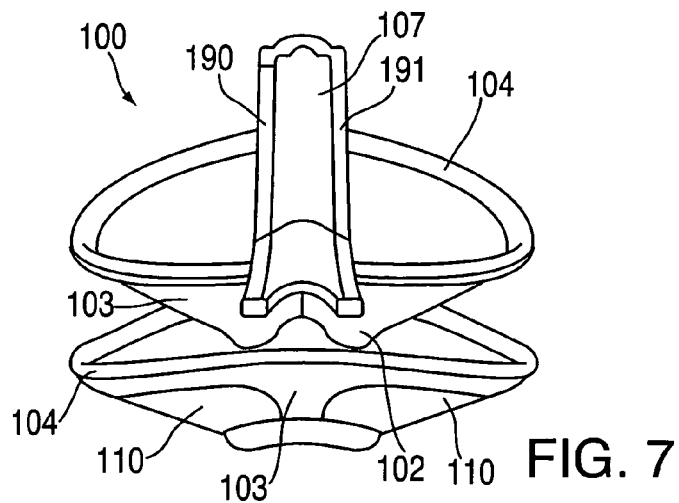
FIG. 7 is a side perspective view similar to FIG. 4 wherein the ear pieces are folded into the storage position as in FIGS. 5 and 6.

FIGS. 5, 6, and 7 are the same views shown in FIGS. 2, 3, and 4 where the earpieces 103 and end band sections 102 are folded inwardly in a storage position. The position shown in FIGS. 2, 3, and 4 is called the deployed position and the folded position shown in FIGS. 5, 6 and 7 is the storage position. In the storage position, the protective ear appliance 100 can be stowed either in a pocket or a small bag or other container without occupying as much space or presenting storage problems.

While FIGS. 5, 6, and 7 show the same ear piece 103 closer to the center band 101, this is merely a matter of choice. The earpieces 103 can be nested with the other earpiece 103 closer to center band 101 without affecting the final size of the protective ear appliance in its storage mode.

Figure 8:
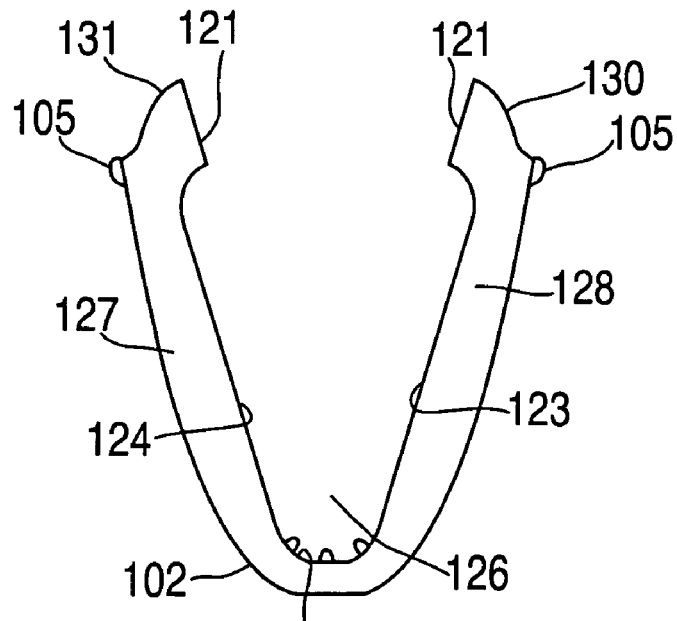
FIG. 8 is a top plan view of the band end piece in its unassembled state.
Figure 9:
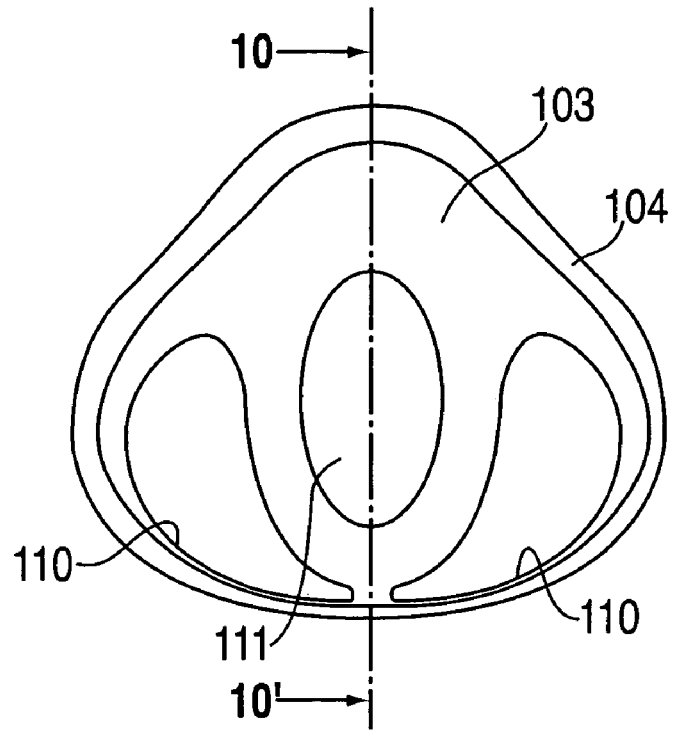
FIG. 9 is a top plan view of an ear piece in accordance with a preferred embodiment of the invention.
Figure 10:
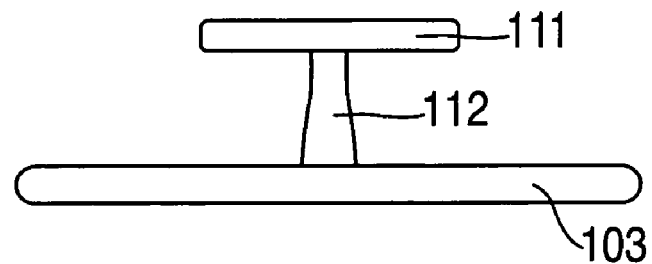
FIG. 10 is a sectional view taken along the line 10-10' of FIG. 9.

As seen in FIG. 4, together with FIGS. 8, 9 and 10, the slideable adjustment of earpiece 103 relative to end band section 102 is performed by a sliding of earpiece 103 relative to a slot 126 in end band section 102. Earpiece 103 has a cap 111, seen in FIGS. 4, 9, and 10 which is supported on a post 112 formed as part of earpiece 103. FIG. 9 shows that the general configuration of earpiece 103 is in the form of a teardrop, and includes two lobe shaped openings 110 which reduce the weight of earpiece 103, increase the flexibility of earpiece 103 in the areas around these openings, and prevent the overheating which is often a component of prior art earmuffs and ear bands. Earpiece cap 111 which sits atop post 112 prevents the earpiece 102 from separating from end band section 102. In a current preferred embodiment, earpiece cap 111 and earpiece post 112 are integrally formed or permanently secured to the remaining portions of earpiece 103. To accommodate this fixed arrangement, end band section 102 is formed n a generally U shaped format shown representationally in FIG. 8.

End band section 102 includes facing end surfaces 121 and 122 shown as the two mating surfaces meeting in a vertical line, and which is also visible in one of the end band portions 102 in FIG. 1. End band section 102 also includes interior slot surfaces 123, 124 which, when assembled, form the interior surface of slot 126. A bendable slot bottom 125 is shown in FIG. 8 which has a thinned bendable slot bottom section 125 which can be bent so as to allow facing end surfaces 121 and 122 to contact each other. In addition, end band section has hinge components 105 on either side of end band section 102 close to the facing end surfaces 121, 122. There are end band slot walls 127 and 128 and also end band hinge adjoining top surfaces 130, 131 which are shaped so as to mate with the curved end of center band section 101 when facing end surfaces 121 and 122 are in contact as shown in FIG. 4.

The assembly of earpiece 103 to end band section 102 is achieved by taking the originally formed U shaped member 102 shown in FIG. 8, causing it to encircle ear piece post 112, below earpiece cap 111 and then closing the U shaped member 102 so that is forms a narrow end band section 102 as shown in FIG. 4 where facing end surfaces 121, 122 are in contact and the slot 126 is generally an oval with curved ends and relatively straight interior slot walls 123, 124. In a preferred embodiment, the facing end surfaces 121, 122 are permanently secured to each other either by welding, gluing, or other conventional means after assembly so that the earpiece 103 will be permanently affixed to end band section 102 although relative motion between the two pieces is possible within the range of motion enabled by the sliding of earpiece post 112 along slot 126.

Generally, earpiece post 112 is sized either with smooth surfaces or with surfaced with teeth so as to slide with a certain amount of friction between the elements so that the earpiece 103 tends to remain in the position to which it is set by the wearer. Different approaches can be utilized which provide defined spacing such as détentes or teeth which would provide more fixed positions of location. However, in the current preferred embodiment, such teeth are not indicated as the pressure of the wearer's head on the band on the tension in the center band and end band sections 101, 102 cause sufficient biasing force by the ear pieces against the ear so as to keep the ear pieces in the appropriate location relative to the wearer's head. In addition, although FIG. 4 is drawn in a vertical orientation, in use, the bands 101, 102 would be oriented in a horizontal fashion and gravity would not tend to cause the ear pieces 103 to move relative to end band sections 102.

Generally, when the earpieces 103 are secured to the end band sections 102, the end band sections 102 are then secured to center band section 101. The connection is achieved by coupling the band portions by use of hinge 105. Several different varieties of hinges can be utilized. One approach is to use a hinge with two interlocking hinge sections formed on the ends of center band 101 and the connecting end of end band sections 102 which are held together by a pin or similar member. Alternatively, and in a current preferred embodiment, a pinless hinge arrangement is formed in which a ball and socket arrangement is enabled with the ball being forced into the socket and thus providing the same pivoting motion without the need for an additional pin element. As shown, a portion of hinge 105 is formed on each end of center band 101 and the other portion is on each of end band sections 102 next to the end band hinge adjoining top surfaces 130, 131. In some current preferred embodiments of the invention the ball and socket approach is further strengthened by sealing at least a portion of the open end of the socket once the ball portion is seated therein so as to prevent the ball from exiting the socket. Alternative hinge arrangements are possibly including use of separate elements to form the hinge in conventional fashion as in eye glasses or similar devices which have hinges.

Openings 110 in earpiece 103 extend through earpiece 103. As it is not appropriate to have an unclosed opening through earpiece 103, a liner 170 is glued or otherwise conventionally affixed to the inside surface of earpiece 103. In the current preferred embodiment, the liner 170 is formed of a die cut piece of fleece material which provides a barrier layer so that air, wind and precipitation do not come directly through the earpiece. In addition, they provide a region of increased sound flow so that the audio insulating effect of a completely closed earpiece is avoided and generally, a color or pattern motif can be shown for purposes of identifying a person's protective ear appliance from those of others. Also high tech fabrics which are windproof, waterproof and/or breathable may be used.

Reference is next made to FIGS. 11-16 wherein the cap 104 is shown in various figures and embodiments. As seen in FIG. 11, the cap 104 includes a stretchable cap frame 140 and a cap membrane 141 secured to the stretchable cap frame 140 by cap membrane stitching 142. The current preferred embodiment is with stitching but an adhesive or ultrasonic welding or other conventional attachment device can be utilized to secure these members. As seen in the cross sectional view of FIG. 12 the stretchable cap frame 140 has a generally V-shaped or U-shaped profile as highlighted in the cross-sectional view of FIG. 12 and can be formed into current preferred embodiments shown as enlarged views FIGS. 12A and 12B. In FIG. 12A stretchable cap frame 140 is sewn to cap membrane 141 with stitching 142 and a generally V-shaped channel 151 is formed which grabs around the edge of earpiece 103 when the cap 104 is in place. Both embodiments have a lip end 147 having a lip end stitching 148 which provides a stop to reduce the possibility that the cap will inadvertently slide off earpiece 103. The difference between the embodiments of FIGS. 12A and 12B are that FIG. 12A has an additional stiffening body 149 which fits within lip 146 and is held in place by stitching 150. The FIG. 12B embodiment does not include this additional stiffening member and the embodiment without the stiffening member of FIG. 12B is the current preferred embodiment.

As shown in FIG. 16 the cap membrane 141 is aligned with cap membrane stitching location 143 between the inner perimeter 144 of stretchable cap frame 140 and outer perimeter 145 of stretchable cap frame 140. FIGS. 14 and 15 show the interior and exterior, respectively, of cap 104 with stretchable cap frame 140 and cap membrane 144 as shown along with cap membrane stitching 142. Finally, FIG. 13 shows the embodiment in which there is the stiff body 149, which is then secured by stiff body stitching 150 in cap 104. Stiff body 149 is preferably formed of a light stiff material like a plaster layer.

In a current preferred embodiment, the stretchable cap frame 140 is formed of a spandex or lycra material which has an inherent stretchability to it and some structural memory and cap membrane 141 can be a natural or synthetic material but in a current preferred embodiment is a brushed polyester material which provides comfort to the wearer's ear as this is the component which rests against the wearer's ear. Natural or synthetic materials may be used. As seen in FIGS. 11 and 12, the portion of the membrane 141 which faces the V-shaped channel 151 does not come in contact with the wearer's ear.

In a current preferred embodiment, the center band 101 and end bands 102 are formed of nylon materials which provide the requisite flexibility, ability to maintain tension, and continued flexibility and tension without brittleness at the low temperature at which an ear protective appliance would ordinarily be worn. The ribs 190, 191 which run parallel to the length of the center band 101 along either edge stiffen the center band to increase the force it exerts on the wearer's head without increasing the weight. Similar ribs 192, 193 continue in end band sections 102. Other materials may be suitably used which might include a polyvinylchloride or polycarbonate and other similar materials which have appropriate resistance to cracking at low temperatures and would provide suitable amounts of tension throughout the length of the band.

Figure 17:
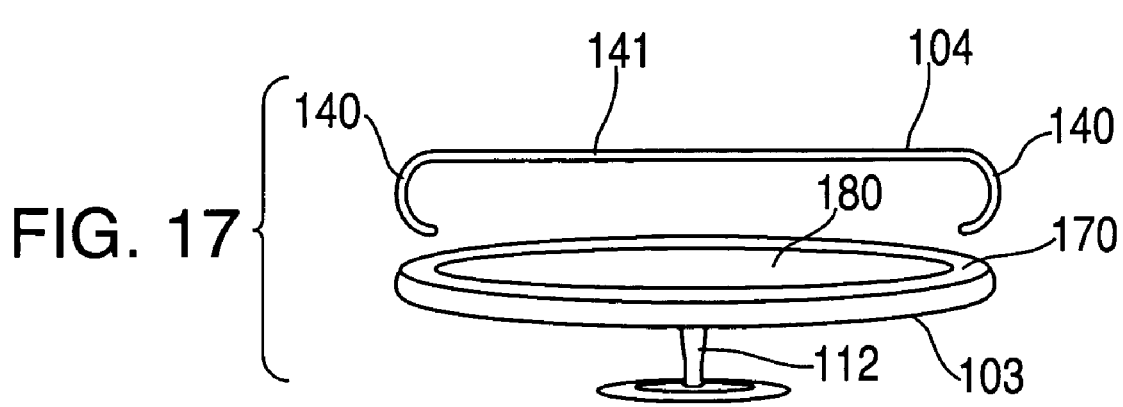
FIG. 17 is an exploded side elevational view of an earpiece and cap in accordance with a preferred embodiment of the invention.

Reference is made to FIG. 17 wherein a schematic view of the different elements in and around earpiece 103. Earpiece 103 appears at the bottom of FIG. 17 with the liner 170 secured to it. An insulation layer 180 which might be a two-ounce or four-ounce insulation or other level of insulation as indicated by the specific needs of the protective ear appliance 100 being produced can be just laid on top of liner layer 170. Liner layer 170 indicated is preferably die cut for improved reliability of sizing but may be cut by other approaches as well. Finally, cap 104 comes on top of insulation layer 180 and maintains insulation layer 180 in place between the cap 140 and earpiece 103. In certain circumstances, the insulation may either by removed or supplemented by additional, greater insulative material. Generally, cap 104 may be removed from ear piece 103 to clean or exchange it for a new cap 104. Alternatively, cap 104 may be affixed permanently to earpiece 103.

Figure 19:
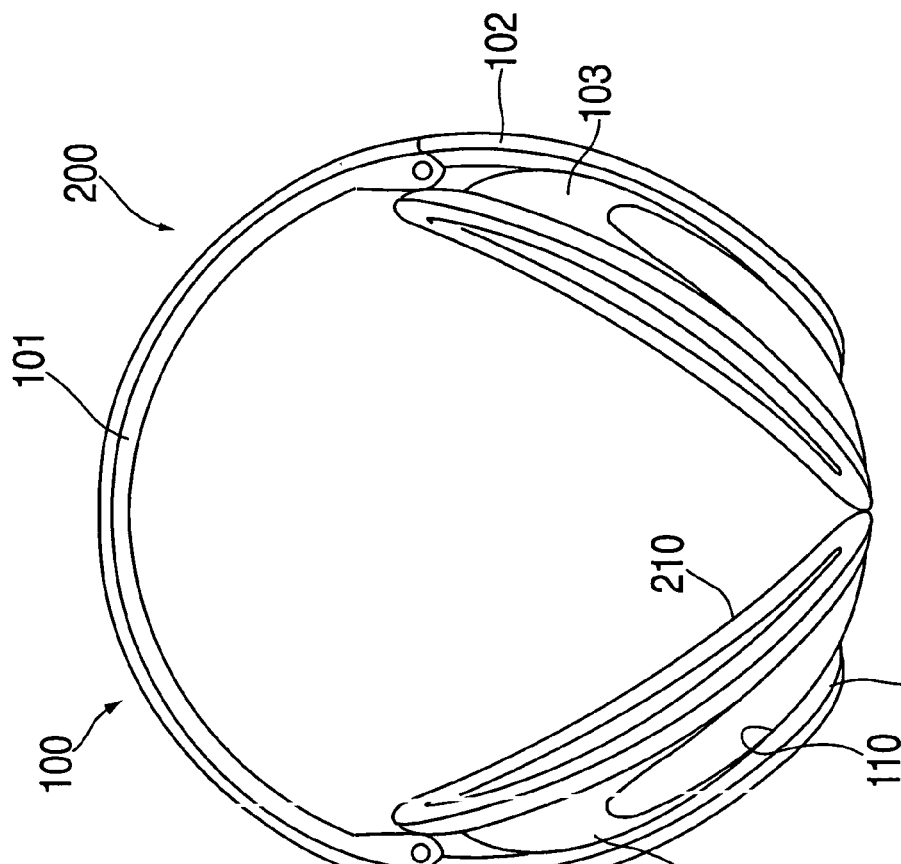
FIG. 19 is a perspective view of the protective ear appliance of FIG. 18 rotated 90 degrees from the perspective of FIG. 18.
Figure 18:
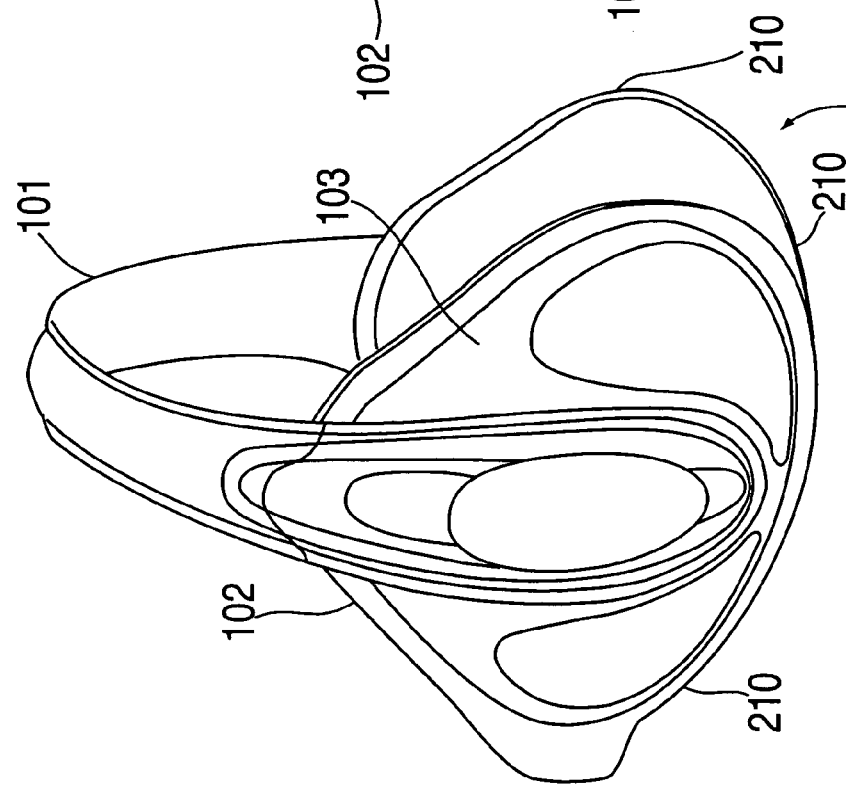
FIG. 18 is a perspective view of a protective ear appliance in accordance with another preferred embodiment of the invention.

Reference is next made to FIGS. 18 and 19 in which a protective ear appliance 200 constructed in accorded with another preferred embodiment of the invention is depicted, like reference numeral representing like elements. Protective ear appliance 200 differs from protective ear appliance 100 by virtue of the presence of a foam insert 210 which is pressed against the inside of earpiece 103 and is secured generally in place by lobe portions of insert piece 210 sized to fit snugly within the openings in the earpiece 110 as best seen in FIG. 18. Generally, the form fitting is adequate to maintain the pieces in registration but to assure this fit is a permanent connection between earpiece 103 and insert piece 210 conventional gluing methods may also be used. Depending upon the materials utilized for foam insert 210 the protective ear appliance 200 can be utilized either with or without a cap. If the foam insert 210 is selected to be sufficiently soft and comfortable to the wearer's ear, it may be used without any cap 104 or, in certain circumstances a cap can be placed over it and an insulating layer 180 added if indicated.

Figure 20:
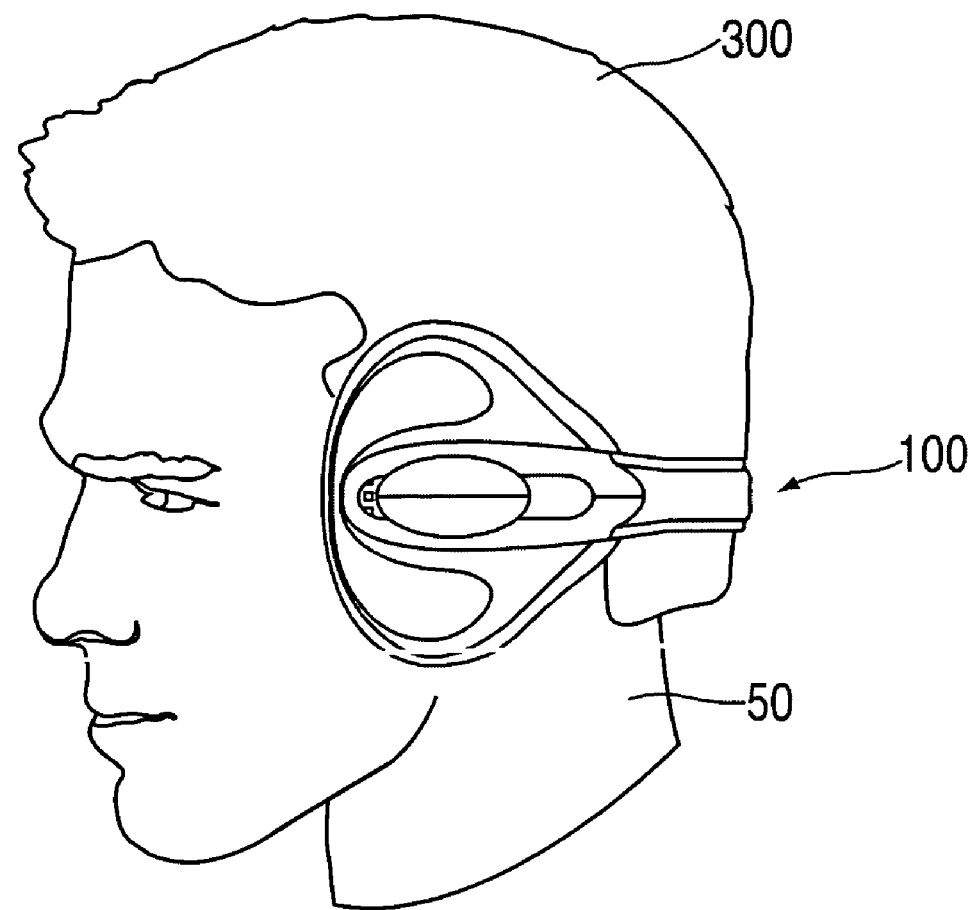
FIG. 20 is a perspective view showing the protective cap appliance in accordance with the invention on a wearer's head.

Finally, reference is made to FIG. 20 wherein a protective ear appliance 100 constructed in accordance with a preferred embodiment of the invention is shown being worn on the back of a wearer's head 50 so as not to disturb the wearer's hair or to allow a hat 300 to be worn without fitting in an unusual fashion.

Accordingly, an improved protective ear appliance is provided which can be worn over the back of the wearer's head and can be independently adjusted to different lengths to fit different sized heads. In addition, the independent adjustment of the ear pieces relative to the band allows for independent adjustment relative to each ear so that if wearer's ears are not aligned in the same place, the protective ear appliance can be appropriately adjusted without affecting the overall fit of the protective ear appliance and the way in which the band sits on the wearer's head.

It will thus be seen that the objects set forth above, among those made apparent in the preceding description, are efficiently obtained and, since certain changes may be made in the above constructions without departing from the spirit and scope of the invention, it is intended that all matter contained in the above description or shown in the accompanying drawings shall be interpreted as illustrative, and not in a limiting sense.

It is also understood that the following claims are intended to cover all of the generic and specific features of the invention herein described and all statements of the scope of the invention, which, as a matter of language might be said to fall therebetween.

What is claimed is:

1. A protective ear appliance, comprising:
    two ear protectors having a generally teardrop shape, the ear protectors each comprising a frame member having an inside surface facing a user's ear and an outside surface facing away from a user's ear with at least two openings therethrough, a liner affixed to the inside surface of the frame member and a removable cover covering the entire inside ear facing surface of the frame member including the openings therethrough, said cover comprising a cover membrane attached to a stretchable cover frame which grabs around the edge of the frame member when the cover is in place;
    a band for encircling a portion of the wearer's head, having a curved shape, with two ends, and an inner curved surface and an outer curved surface;
    slidable coupling means for slidably coupling each of the ear protectors to the band so that the ear protectors can each slide independently with respect to the band to adjust the distance between the two ear protectors along the band so that the ear protectors can seat on the wearer's ears.

2. The protective ear appliance of claim 1 further including hinge means for folding end portions of the band relative to the rest of the band, wherein the hinge means folds an end portion at both ends of the band, defining a central portion of the band and two end portions.

3. The protective ear appliance of claim 2 wherein each end portion of the band beyond the hinge means moves between a deployed positions where the end portions of the band continue the curved shape of the central portion of the band and a storage position where the end portions of the band are folded within the inner curved surface of the central portion.

4. The protective ear appliance of claim 3 wherein the ear protector coupled to each end portion of the band moves between the deployed position and the storage position along with the corresponding end portion of the band.

5. The protective ear appliance of claim 4 wherein the end portions of the band and the ear protectors fit within the central portion of the band when the end portions are in the storage position.

6. The protective ear appliance of claim 2 wherein the hinge means is formed on either end of the central band and on the end of each end portion of the band.

7. The protective ear appliance of claim 6 wherein the hinge means also keeps the two end portions secured to the central band portion.

8. The protective ear appliance of claim 1 wherein the slidable coupling means couples each of the ear protectors to one of the end portions of the band.

9. The protective ear appliance of claim 8 wherein the slidable coupling means includes a slot formed through each of the end portions of the band, from the inner curved surface to the outer curved surface.

10. The protective ear appliance of claim 9 wherein the slidable coupling means further includes an engaging member on each ear protector which extends through a corresponding slot in a corresponding end portion of the band and has a cap on the engaging member to prevent the engaging member from moving out of the corresponding slot.

11. The protective ear appliance of claim 10 wherein the cap is permanently fixed to the engaging member.

12. The protective ear appliance of claim 10 further comprising restrictive means having fixed points of interaction for discrete adjustments disposed in the slidable coupling means for providing frictional resistance between the ear protectors and the end portions of the band so that continuous adjustments in the distance between the ear protectors around the back of the wearer's head is enabled.

13. The protective ear appliance of claim 12 wherein the fixed points of interaction for discrete adjustments comprise teeth or détentes between the slot and the engaging member.

14. The protective ear appliance of claim 10 wherein each slot defines a range of motion relative to the ends of the band along the direction of the ends of band.

15. The protective ear appliance of claim 14 wherein the ear protectors fit over the wearer's ears and the band encircles the back of the wearer's head between the ears.

16. The protective ear appliance of claim 1 wherein the frame member of the ear protector is formed as a two piece interlocking member.

17. The protective ear appliance of claim 16 wherein one of the interlocking members includes the engaging member and a cap and the second of the interlocking members includes a portion of the ear protector which rests against the wearer's ear.

18. The protective ear appliance of claim 17 wherein the ear protector is formed as a frame member including the engaging member and the cap and the cover is held around a perimeter of the frame member.

19. The protective ear appliance of claim 18 wherein the frame member is made in a mold and has at least two openings from an inner surface to an outer surface.

20. The protective ear appliance of claim 1 wherein the stretchable cover frame has an elasticized edge which holds onto the ear protectors.

21. The protective ear appliance of claim 20 further including insulation between the cover and the frame member.

22. The protective ear appliance of claim 1 wherein the openings are sized to allow heat to escape from a wearer's head.

23. The protective ear appliance of claim 1 wherein the openings are sized to increase the flexibility of the ear protectors.

24. The protective ear appliance of claim 1 wherein the openings are sized to decrease the weight of the ear protectors.

25. The protective ear appliance of claim 1 wherein the band includes ribs running along the length of the band.

26. The protective ear appliance of claim 25 wherein there are two ribs extending along the band.

27. The protective ear appliance of claim 1 wherein the frame member of the ear protector is formed as a two piece interlocking member.

28. The protective ear appliance of claim 1 wherein the frame member of the ear protector comprises an engaging member and a cap and the cover is held around a perimeter of the frame member.

* * * * *